(12) United States Patent
Ozeki et al.

(10) Patent No.: US 9,207,183 B2
(45) Date of Patent: Dec. 8, 2015

(54) STIMULATED RAMAN SCATTERING MEASUREMENT APPARATUS

(71) Applicant: CANON KABUSHIKI KAISHA, Tokyo (JP)

(72) Inventors: Yasuyuki Ozeki, Minoh (JP); Kazuyoshi Itoh, Kawanishi (JP); Wataru Umemura, Suita (JP)

(73) Assignee: CANON KABUSHIKI KAISHA (JP)

( * ) Notice: Subject to any disclaimer, the term of this patent is extended or adjusted under 35 U.S.C. 154(b) by 306 days.

(21) Appl. No.: 13/683,320

(22) Filed: Nov. 21, 2012

(65) Prior Publication Data
US 2013/0135615 A1    May 30, 2013

(30) Foreign Application Priority Data
Nov. 25, 2011  (JP) ................. 2011-257894

(51) Int. Cl.
*G01J 3/44* (2006.01)
*G01N 21/65* (2006.01)
*G01J 3/10* (2006.01)
(Continued)

(52) U.S. Cl.
CPC . *G01N 21/65* (2013.01); *G01J 3/10* (2013.01); *G01J 3/4338* (2013.01); *G01J 3/44* (2013.01); *H01S 3/1307* (2013.01); *G01N 2021/655* (2013.01); *H01S 3/0078* (2013.01); *H01S 3/0092* (2013.01); *H01S 3/06754* (2013.01);
(Continued)

(58) Field of Classification Search
CPC ............. G01N 2021/655; G01N 21/65; H01S 3/0078; H01S 3/0092
See application file for complete search history.

(56) References Cited

U.S. PATENT DOCUMENTS 6,151,522 A * 11/2000 Alfano et al. ................. 600/473
7,106,436 B1    9/2006 Gord et al.
(Continued)

FOREIGN PATENT DOCUMENTS

JP    2009180706 A    8/2009
JP    2010-048805 A    3/2010
(Continued)

OTHER PUBLICATIONS

Krauss, Günther, et al. "Compact coherent anti-Stokes Raman scattering microscope based on a picosecond two-color Er: fiber laser system." Optics letters 34.18 (2009): 2847-2849.*
(Continued)

*Primary Examiner* — Kara E Geisel
*Assistant Examiner* — Rufus Phillips
(74) *Attorney, Agent, or Firm* — Rossi, Kimms & McDowell LLP (57) ABSTRACT

The measurement apparatus combines first and second lights from first and second light generators to focus the combined light to a sample, and detect the first or second light intensity-modulated by stimulated Raman scattering. The first light generator includes a light dispersion element separating the light from a light introducing optical system in different directions according to light frequencies, and drives at least one of the light dispersion element and part of the light introducing optical system so as to change an incident angle of the light to the light dispersion element to extract part of the separated light, thereby making a light frequency of the first light variable. The second light generator produces a plurality of the second lights having mutually different light frequencies. The apparatus measures a Raman spectrum by changing the light frequency of the first light.

16 Claims, 7 Drawing Sheets

(51) Int. Cl.
 *G01J 3/433* (2006.01)
 *H01S 3/13* (2006.01)
 H01S 3/00 (2006.01)
 H01S 3/067 (2006.01)
 H01S 3/16 (2006.01)
 H01S 3/23 (2006.01)

(52) U.S. Cl.
 CPC ............ *H01S3/1611* (2013.01); *H01S 3/1618* (2013.01); *H01S 3/2391* (2013.01)

(56) References Cited

U.S. PATENT DOCUMENTS

| | | | |
|---|---|---|---|
| 7,991,022 B1 * | 8/2011 | Soh et al. | 372/3 |
| 2006/0066848 A1 * | 3/2006 | Frankel | 356/301 |
| 2010/0046039 A1 | 2/2010 | Xie et al. | |
| 2011/0122407 A1 * | 5/2011 | Jalali et al. | 356/301 |
| 2011/0128538 A1 * | 6/2011 | Cerullo et al. | 356/301 |
| 2012/0326037 A1 | 12/2012 | Ohtake et al. | |

FOREIGN PATENT DOCUMENTS

| | | | |
|---|---|---|---|
| JP | 2011106990 A | 6/2011 | |
| JP | 2011175093 A | 9/2011 | |
| JP | 2011196990 A | 10/2011 | |
| WO | 2010140614 A1 | 12/2010 | |

OTHER PUBLICATIONS

Official Action issued in JP2011-257894 mailed Sep. 24 2014.
Fumihiro Dake et al., "Principle confirmation of stimulated Raman scattering microscopy" (Optics&Photonics Japan 2008, 5pC12).
Freudige et al. "Label-free biomedical imaging with high sensitivity by stimulated Raman scattering microscopy" (Science vol. 322 Dec. 19, 2008 pp. 1857-1861).
"Label-Free and Real-Time Monitoring of Biomass Processing with Stimulated Raman Scattering Microscopy" along with Supporting Information (published by Harvard University as a research paper in 2010).
"Fiber-format stimulated-Raman-scattering microscopy from a single laser oscillator" (published by Politecnico di Milano as a research paper in 2010).
Berger J. et al. "Widely Tunable, Narrow Optical Bandpass Gaussian Filter Using a Silicon Microactuator", Tuesday Afternoon. pp. 252-253, vol. 1/OFC 2003.
Extended European Search Report issued in European counterpart application No. EP12193755.1, dated Feb. 21, 2013.
Office Action Issued in Counterpart JP2011257894, dated Jun. 10, 2014.

* cited by examiner

STIMULATED RAMAN SCATTERING MEASUREMENT APPARATUS

BACKGROUND OF THE INVENTION

1. Field of the Invention

The present invention relates to a stimulated Raman scattering measurement apparatus performing molecular vibration imaging by utilizing stimulated Raman scattering, the apparatus being particularly suitable for a microscope, an endoscope and the like.

2. Description of the Related Art

A stimulated Raman scattering (SRS) measurement apparatus that is one of measurement apparatuses utilizing a Raman scattering principle has been proposed in "Principle confirmation of stimulated Raman scattering microscopy" (Optics&Photonics Japan 2008, 5pC12) by Fumihiro Dake, Yasuyoki Ozeki and Kazuyoshi Ito and "Label-free biomedical imaging with high sensitivity by stimulated Raman scattering microscopy" (SCIENCE VOL322 19 Dec. 2008 pp. 1857-1861) by Chiristian W. Freudiger, Wei Min, Brian G. Saar, Sijia Lu, Gary R. Holtom, Chengwei He, Jason C. Tsai, Jing X. Kang and X. Sunney Xie. The principle of the SRS detection apparatus is as follows.

When two light pulses whose light frequencies are mutually different are focused to a sample, a coincidence of difference between the light frequencies of the two light pulses with a molecular vibration frequency of the sample causes a phenomenon of stimulated Raman scattering at a light-focused point. The stimulated Raman scattering decreases intensity of one of the two light pulses having a higher light frequency, and increases intensity of the other one having a lower light frequency. Detection of such intensity change enables molecular vibration imaging in which vibration information of molecules of the sample is reflected. In this detection, performing intensity modulation on one of the two light pulses or providing to the one light pulse a repetition frequency that is an integral multiple of that of the other light pulse modulates the intensity change caused by the stimulated Raman scattering. Therefore, detecting the modulation of the intensity change of the other light pulse (on which the intensity modulation is not performed) by a lock-in amplifier enables detection of the stimulated Raman scattering with high sensitivity.

For such a stimulated Raman scattering measurement apparatus, it is expected that its discrimination ability for the sample may further improve, not by detecting the molecular vibration only at a specific light frequency, but by detecting a molecular vibration spectrum (hereinafter referred to as "a Raman spectrum") in a wide vibration frequency range. Japanese patent Laid-Open No. 2010-48805 and "Label-Free and Real-Time Monitoring of Biomass Processing with Stimulated Raman Scattering Microscopy (Supporting Information)" (published by Harvard University as a research paper in 2010) disclose stimulated Raman scattering measurement apparatuses capable of scanning the light frequency of one of the above-mentioned two light pulses by using one or more optical parametric oscillators (hereinafter referred to as an "OPO") having an oscillation wavelength variable function.

The OPO can scan a comparatively wide light frequency range by changing not only a tilt of a crystal that outputs the above one light pulse, but also temperature thereof. Moreover, "Fiber-format stimulated-Raman-scattering microscopy from a single laser oscillator" (published by Politecnico di Milano as a research paper in 2010) discloses a stimulated Raman scattering measurement apparatus capable of scanning the light frequency of one of the above two light pulses by changing temperature of a periodically poled element, such as periodically poled lithium niobate (PPLN), from which the one light pulse exits.

However, the stimulated Raman scattering measurement apparatuses disclosed in Japanese patent Laid-Open No. 2010-48805, "Label-Free and Real-Time Monitoring of Biomass Processing with Stimulated Raman Scattering Microscopy (Supporting Information)" and "Fiber-format stimulated-Raman-scattering microscopy from a single laser oscillator" gradually perform scanning of the light frequency by changing the temperature of the crystal in the OPO or of the periodically poled element, so that it takes a long time to acquire the Raman spectrum in a wide light frequency range. As methods for performing the scanning in a wide light frequency range in a short time, there are known a method of filtering wideband laser light by an acoustooptic tunable filter (AOTF) and a method of providing a chirp to two laser light pulses whose light frequencies are mutually different and controlling a time difference between the pulses to change a molecular vibration frequency. However, these methods cannot provide sufficient spectral resolution in the stimulated Raman scattering measurement apparatus.

SUMMARY OF THE INVENTION

The present invention provides a stimulated Raman scattering measurement apparatus capable of acquiring the Raman spectrum with high resolution and at high speed.

The present invention provides as one aspect thereof a stimulated Raman scattering measurement apparatus including a first light generator configured to produce a first light, a second light generator configured to produce a second light having a light frequency different from that of the first light, an optical system configured to combine the first light with the second light to focus the combined first and second lights to a sample, and a detector configured to detect the first or second light intensity-modulated by stimulated Raman scattering caused by the focusing of the combined first and second lights to the sample. The first light generator includes a light introducing optical system and a light dispersion element, the light introducing optical system introducing light from a first light source to the light dispersion element, and the light dispersion element being operable to separate the light introduced thereto in different directions according to light frequencies. The first light generator is configured to drive at least one of the light dispersion element and an optical element included in the light introducing optical system so as to change an incident angle of the light from the first light source to the light dispersion element to extract part of the separated light in the mutually different directions, thereby being configured to make a light frequency of the first light variable. The second light generator is configured to produce a plurality of the second lights having mutually different light frequencies by using light from at least one second light source. The apparatus is configured to measure a Raman spectrum by changing the light frequency of the first light.

Further features of the present invention will become apparent from the following description of exemplary embodiments with reference to the attached drawings.

DESCRIPTION OF THE PREFERRED EMBODIMENTS

Exemplary embodiments of the present invention will hereinafter be described with reference to the accompanying drawings.

Embodiment 1

Figure 1:
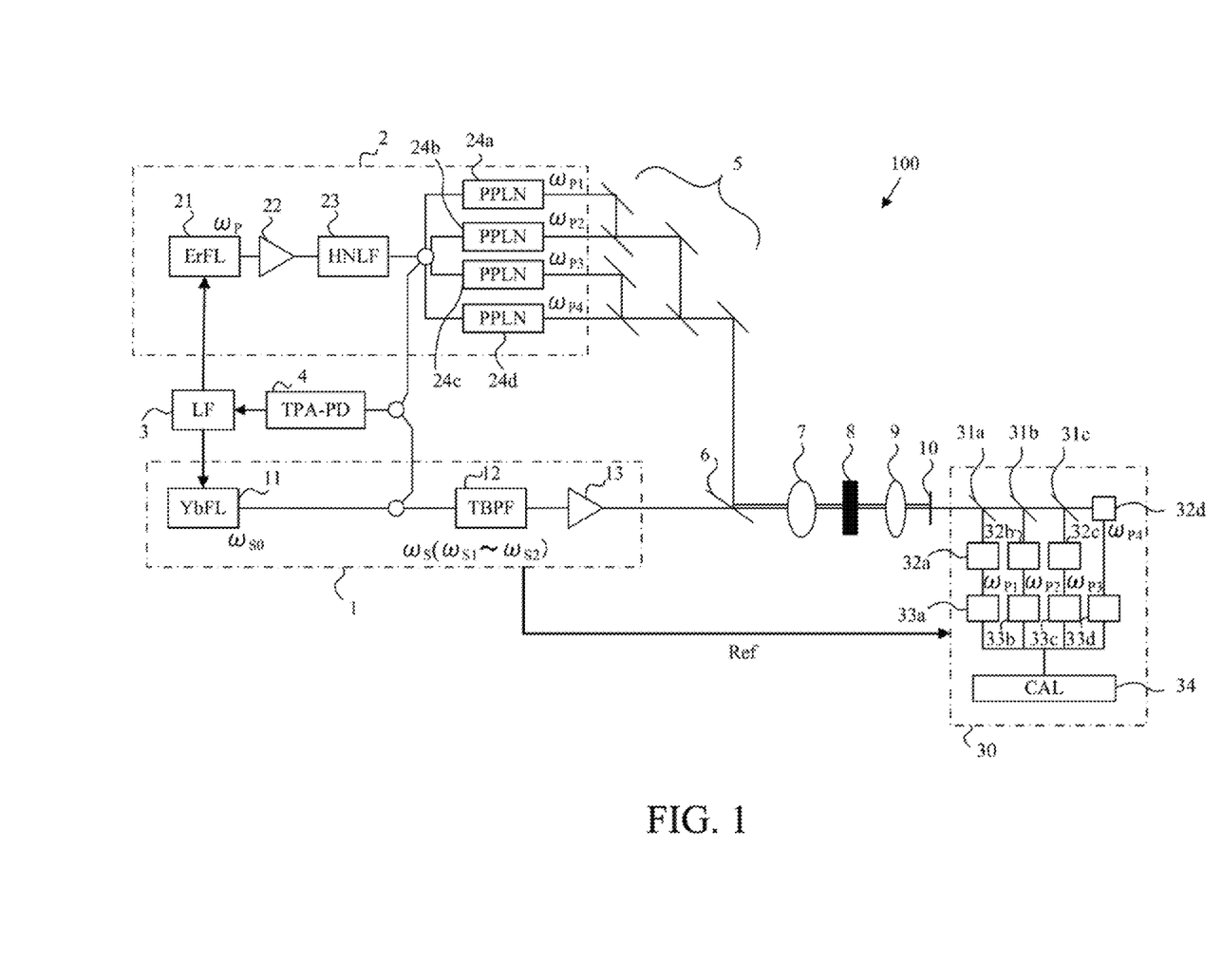
FIG. 1 is a block diagram showing a configuration of a stimulated Raman scattering measurement apparatus that is Embodiment 1 of the present invention.

FIG. 1 shows a configuration of a stimulated Raman scattering (SRS) measurement apparatus that is a first embodiment (Embodiment 1) of the present invention. The SRS measurement apparatus 100 of this embodiment can be used as apparatuses, such as a microscope and an endoscope, for observation, measurement, diagnosis and other usages.

The SRS measurement apparatus 100 of this embodiment includes a first pulse light generator 1 configured to produce a first pulse light (first light) to be used as a Stokes light and a second pulse light generator 2 configured to produce a second pulse light (second light) to be used as a pump light. Moreover, the measurement apparatus 100 includes a loop filter (LF) 3 and a two-photon absorption photodiode (TPA-PD) 4, which are provided to control emission timings of light sources (described later) provided in the first and second pulse light generators 1 and 2. In addition, the measurement apparatus 100 includes a mirror group 5, a combining mirror (combining element) 6, a first optical system 7, a second optical system 9, a color filter 10 and a light detector 30. A sample 8 that is a measurement target object is installed between the first optical system 7 and the second optical system 9.

The first pulse light generator 1 is constituted of a first light source 11, a wavelength tunable (that is, light frequency variable) band-pass filter (TBPF) 12 and a Yb doped fiber amplifier (YDFA) 13. The first light source 11 repeats emission (oscillation) of a pulse light with a first pulse period, and is constituted of a mode-locked Yb fiber laser (YbFL) in this embodiment. The pulse light emitted from the first light source 11 has, for example, a central light frequency of $\omega_{S0}$ (that is, a wavelength of 1030 nm) and a repetition frequency ($v_S$) of 17.5 MHz.

The wavelength tunable band-pass filter 12 varies a light frequency $\omega_S$ of the pulse light entering thereto from the first light source 11 between $\omega_{S1}$ and $\omega_{S2}$ ($\omega_{S1} < \omega_{S2}$). A configuration of the wavelength tunable band-pass filter 12 will be described later. The Yb doped fiber amplifier 13 amplifies the pulse light exiting from the wavelength tunable band-pass filter 12. The first pulse light thus amplified by the Yb doped fiber amplifier 13 and having the light frequency of $\omega_S$ variable between $\omega_{S1}$ and $\omega_{S2}$ exits from the first pulse light generator 1.

Description will be made of the configuration of the wavelength tunable band-pass filter 12 with reference to FIG. 3. The wavelength tunable band-pass filter 12 is constituted of a light introducing optical system, a light dispersion element 125 and a fiber collimator 126. The light introducing optical system is constituted of a half mirror 121, a light deflecting element 122, a first lens 123 and a second lens 124. The first lens 123 has a focal length of f1, and the second lens 124 has a focal length of f2.

The pulse light from the first light source (YbFL) 11 is transmitted through the half mirror 121 to enter the light deflecting element 122 which is movable. The light deflecting element 122 is constituted of an optical element that is rotatable or swingable at high speed and is operable to change a direction of the light exiting therefrom, such as a galvanic mirror, a polygon mirror, a resonance scanner or a MEMS (Micro-Electro Mechanical Systems) mirror. A driver 128 includes an actuator to rotate (swing) the light deflecting element 122 and an electronic circuit to drive the actuator.

The pulse light reflected by the light deflecting element 122 is transmitted through the first and second lenses 123 and 124 to be introduced to the light dispersion element 125. The light deflecting element 122 changes, by its light deflecting action, an incident angle of the pulse light entering thereto, as shown by solid lines and dotted lines in FIG. 3.

The light dispersion element 125 is operable to separate the entering light (pulse light) in different directions according to light frequencies. This embodiment (and also Embodiment 2 described later) uses an element having a diffraction grating as the light dispersion element 125. Use of a dispersion effect of the diffraction grating can sufficiently narrow a spectral width of the first pulse light. As the light dispersion element, other elements such as a prism may be used.

In this embodiment, a distance between the light deflecting element 122 and the first lens 123 and a distance between the first lens 123 and its posterior focal point position are coincident with the focal length f1 of the first lens 123. Moreover, a distance between the second lens 124 and its anterior focal point position and a distance between the second lens 124 and the light dispersion element 125 are coincident with the focal length f2 of the second lens 124. This configuration constitutes a 4f imaging system. Therefore, regardless of the light deflecting action of the light deflecting element 122, the pulse light as a collimated light enters the light dispersion element 125 without change of its entrance point on the light dispersion element 125. In addition, even though the light frequency of the pulse light exiting from the light dispersion element 125 is changed, group delay (group velocity) thereof is kept constant.

The pulse light exiting from the light dispersion element 125 (reflected thereby in Littrow reflection) and having the light frequency $\omega_S$ (from $\omega_{S1}$ to $\omega_{S2}$) according to its incident angle to the light dispersion element 125 is again transmitted through the second and first lenses 124 and 123 and the light deflecting element 122 to enter the half mirror 121. Then, the pulse light is reflected by the half mirror 121 to enter the fiber collimator 126. Thus, part of the light separated by the light dispersion element 125 in the different directions is extracted. The pulse light collimated by the fiber collimator 126 exits therefrom toward the Yb doped fiber amplifier 13.

If the Yb doped fiber amplifier 13 has a problem that the group delay is varied according to the light frequency of the first pulse light, compensation therefor can be made by changing the distance between the second lens 124 and the light dispersion element 125. Moreover, using the Yb doped fiber amplifier 13 in a state where its gain is saturated can suppress variation of output from the Yb doped fiber amplifier caused by scanning of the light frequency of the first pulse light.

In FIG. 1, the second pulse light generator 2 includes a second light source 21, an Er doped fiber amplifier (EDFA) 22, a highly nonlinear fiber (HNLF) 23 and plural (four in this embodiment) periodically poled elements 24a to 24d each constituted of periodically poled lithium niobate (PPLN). The second light source 21 repeats emission (oscillation) of a pulse light with a second pulse period, and is constituted of a mode-locked Er fiber laser (ErFL) in this embodiment. The pulse light emitted from the second light source 21 has, for example, a central light frequency of cop (that is, a wavelength of 1550 nm) and a repetition frequency ($2v_S$) of 35 MHz, which are different from those of the pulse light emitted from the first light source 11.

The Er doped fiber amplifier (EDFA) 22 amplifies the pulse light emitted from the second light source 21 to cause the amplified pulse light to exit therefrom.

The highly nonlinear fiber 23 expands a light frequency band of the pulse light amplified by the Er doped fiber amplifier 22 to convert the pulse light into a supercontinuum (SC) pulse light. The periodically poled lithium niobate elements 24a to 24d serve as harmonic generation elements that respectively generate second harmonics of plural (four) pulse light components included in the SC pulse light from highly nonlinear fiber 23 and having mutually different light frequencies $\omega_{p1}$, $\omega_{p2}$, $\omega_{p3}$ and $\omega_{p4}$. The four second harmonics generated by the periodically poled lithium niobate elements 24a to 24d exit from the second pulse light generator 2 simultaneously with one another as four second pulse lights having the mutually different light frequencies $\omega_{p1}$, $\omega_{p2}$, $\omega_{p3}$, and $\omega_{p4}$. In this embodiment, the light frequencies have the following relationship:

$$\omega_{p1} < \omega_{p2} < \omega_{p3} < \omega_{p4}.$$

This embodiment sets the repetition frequency of the first pulse light to half of the repetition frequency of the second pulse light. Therefore, each light pulse of the first pulse light is produced at a timing synchronizing with a timing corresponding to two light pulses of the second pulse light. Such setting of the production timing of the first pulse light enables increase (maximization) of occurrence frequency of the above-mentioned effect of the stimulated Raman scattering as compared with a case of setting the repetition frequency of the first pulse light to ⅓ or ¼ of that of the second pulse light, which makes it possible to acquire molecular vibration images of the sample 8 with higher accuracy. However, the repetition frequency of the first pulse light is not limited to half of that of the second pulse light, and may be set to ½n (n is an integer equal to or more than 2) such as ¼. Moreover, the repetition frequency of the first pulse light only has to be lower than that of the second pulse light. In other words, it is only necessary to be able to detect the second pulse light intensity-modulated by the stimulated Raman scattering by matching timings at which the first and second pulse lights are focused to the sample 8.

The two-photon absorption photodiode (TPA-PD) photoelectrically converts the pulse light emitted from the first light source 11 and the pulse light emitted from the second light source 21 and transmitted through the highly nonlinear fiber 23 to output a voltage signal showing a timing difference between these pulse lights. The voltage signal showing the timing difference is input to the first and second light sources 11 and 21 through the loop filter 3. Internal circuits of the first and second light sources 11 and 21 control pulse light emission timings thereof so as to make the voltage signal constant, that is, so as to provide the above-mentioned synchronized timings.

Although this embodiment uses, for the first and second light sources 11 and 12, the mode-locked Yb or Er fiber laser, other fiber lasers or lasers other than fiber lasers (such as titanium sapphire laser) may be used.

Moreover, although this embodiment uses the first pulse light having a lower repetition frequency than that of the second pulse light as the Stokes light, and uses the second pulse light as the pump light, the first pulse light may be used as the pump light and the second pulse light may be used as the Stokes light.

The four second pulse lights exiting from the second pulse light generator 2 are introduced to the combining mirror 6 by the mirror group 5, which is constituted of plural dichroic mirrors and plural mirrors, to be concentrically combined with the first pulse light exiting from the first pulse light generator 1. The combined pulse light (first and second pulse lights) is focused to the sample 8 through the first optical system 7.

When the repetition frequencies of the first and second pulse light focused to the sample 8 are respectively represented by $v_S$ and $2v_S$, focusing of both the first pulse light and the second pulse lights (four second pulse lights) to the sample 8 and focusing of only the second pulse light are alternately performed at a time interval of $1/(2v_S)$. At each time where both the first and second pulse lights are focused to the sample 8 at a time interval of $1/v_S$ in a state where difference between the light frequencies of the first and second pulse lights, that is, $\omega_{pn} - \omega_S$ (n=1 to 4) is coincident with a molecular vibration frequency of a measurement target molecule in the sample 8, the stimulated Raman scattering is generated. This stimulated Raman scattering causes intensity modulation of the second pulse light at a frequency of $v_S$.

The first pulse light and the four second pulse lights intensity-modulated by the stimulated Raman scattering exit from the sample 8 and then are collected by the second optical system 9. The first and second pulse lights collected by the second optical system 9 enter the color filter 10. Of these entering pulse lights, only the four second pulse lights are transmitted through the color filter 10 to enter the light detector 30.

The light detector 30 includes three dichroic mirrors 31a to 31c operable to separate the four pulse lights according to their light frequencies, and photodiodes 32a to 32d operable to photoelectrically convert the separated four pulse lights into electric signals (output signals) corresponding to their light intensities. Furthermore, the light detector 30 includes four lock-in amplifiers 33a to 33d into which the output signals from the four photodiodes 11 are respectively input. The four lock-in amplifiers 33a to 33d synchronously detect the output signals from the four photodiodes 11 with a lock-in frequency of $v_S$ shown by a frequency reference signal Ref from the first pulse light generator 1.

Thereby, only light (intensity-modulated component of the second pulse light) caused by the stimulated Raman scattering is detected. Then, scanning an area on the sample 8 to which the first and second pulse lights are focused makes it possible for a calculating unit 34 taking in outputs from the lock-in amplifiers 33a to 33d to acquire a molecular vibration image of the measurement target molecule in the sample 8. In the scanning, the light frequency $\omega_S$ (from $\omega_{S1}$ to $\omega_{S2}$) of the first pulse light is changed (in other words, scanned) with respect to the respective light frequencies $\omega_{p1}$, $\omega_{p2}$, $\omega_{p3}$ and $\omega_{p4}$ of the four second pulse lights enables acquisition of a molecular vibration image and a Raman spectrum in a continuous and wide frequency range.

Figure 6A:
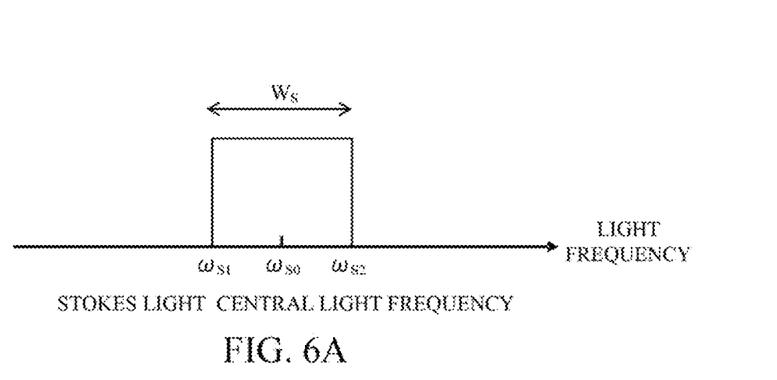
FIGS. 6A to 6C show light frequency scanning in the stimulated Raman scattering measurement apparatus of Embodiment 1.
Figure 6B:
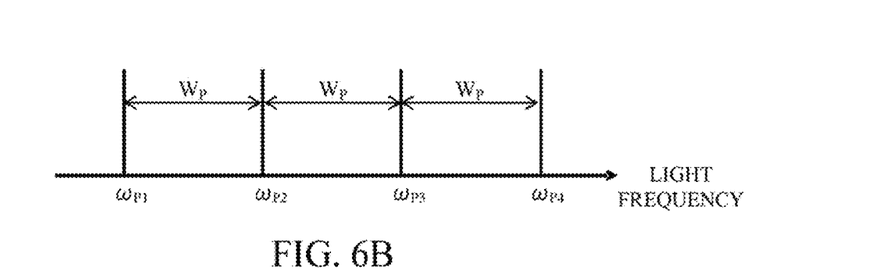

FIG. 6A shows that the light frequency $\omega_S$ (central light frequency $\omega_{S0}$) of the first pulse light exiting from the first pulse light generator 1 is scanned by the wavelength tunable band-pass filter 12 within a variable range $W_s$ from $\omega_{S1}$ to $\omega_{S2}$. FIG. 6B shows the four second pulse lights exiting from the second pulse light generator 2 and having the frequencies $\omega_{p1}$, $\omega_{p2}$, $\omega_{p3}$ and $\omega_{p4}$.

When $W_P$ represents a frequency pitch that is difference among the frequencies $\omega_{p1}$, $\omega_{p2}$, $\omega_{p3}$ and $\omega_{p4}$ of the four second pulse lights, it is desirable that the variable range (scanning width) $W_S$ of the light frequency of the first pulse light be equal to or more than W.

Figure 6C:
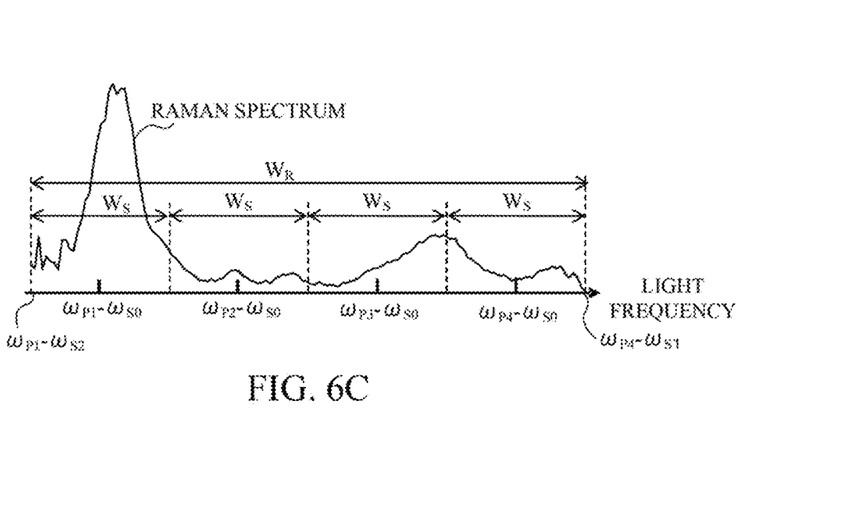

As shown in FIG. 6C, scanning of the light frequency of the first pulse light with respect to the light frequencies of the four second pulse lights enables detection of the Raman spectrum in a continuous and wide vibration frequency range $W_R$ from a vibration frequency of $\omega_{p1}-\omega_{S2}$ to a vibration frequency of $\omega_{p4}-\omega_{S1}$. FIG. 6C shows a case where the scanning width $W_S$ of the light frequency of the first pulse light is coincident with $W_P$.

If a target spectrum range (predetermined light frequency range) for the detection of the Raman spectrum is decided, the scanning width of the light frequency of the first pulse light and the number and light frequencies of the second pulse lights will be selected so as to enable the scanning in this target spectrum range.

This embodiment scans the light frequency of the first pulse light with respect to the respective light frequencies of the plural second pulse lights simultaneously exiting from the second pulse light generator 2 by utilizing high speed rotation of the light deflecting element 122 in the wavelength tunable band-pass filter 12. Therefore, this embodiment enables high speed scanning, and thereby makes it possible to acquire the Raman spectrum in a wide vibration frequency range in a short time.

Moreover, this embodiment sufficiently narrows the spectral width of at each scan point light frequency of the first pulse light by the wavelength tunable band-pass filter 12, so that this embodiment enables detection of the Raman spectrum with high resolution.

Figure 7:
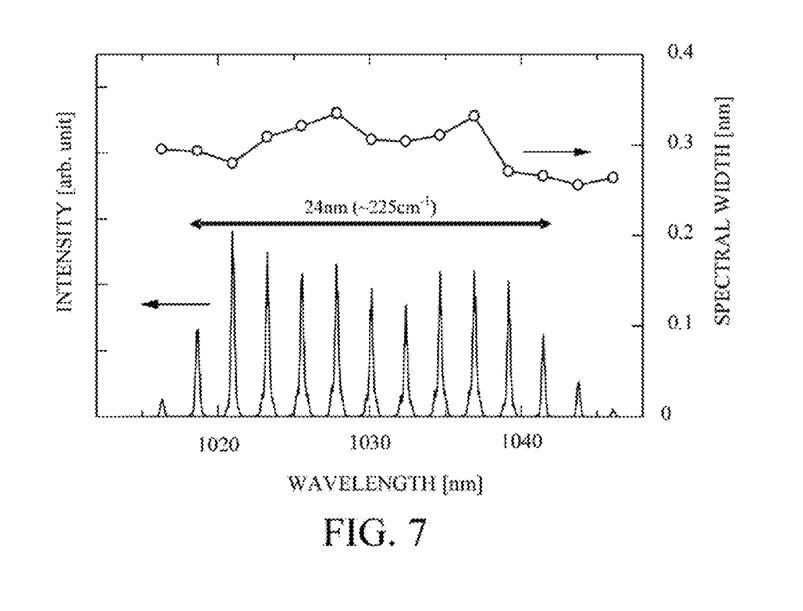
FIG. 7 shows a result of the light frequency scanning of the first pulse light obtained by an experiment using the stimulated Raman scattering measurement apparatus of Embodiment 1.

FIG. 7 shows an experiment example of the scanning of the light frequency of the first pulse light using the wavelength tunable band-pass filter 12 described in this embodiment. This experiment resulted in 24 nm as an effective scanning width of the light frequency of the first pulse light, and resulted in 0.3 nm as the spectral width at each scan point light frequency. This spectral width is sufficiently narrow for the high resolution detection of the Raman spectrum.

Figure 8:
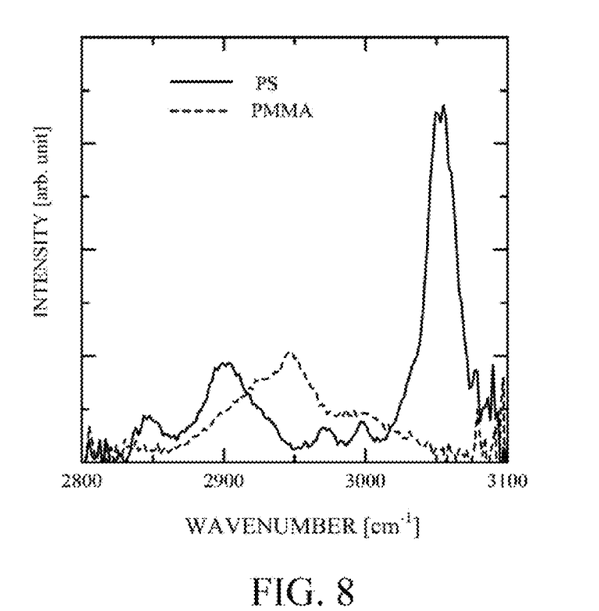
FIG. 8 shows an image obtained by an experiment using the stimulated Raman scattering measurement apparatus of Embodiment 1.
Figure 9A:
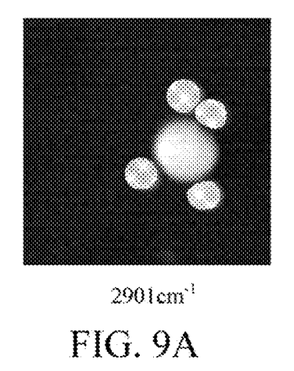
FIGS. 9A to 9D show Raman spectra obtained by experiments using the stimulated Raman scattering measurement apparatus of Embodiment 1.
Figure 9B:
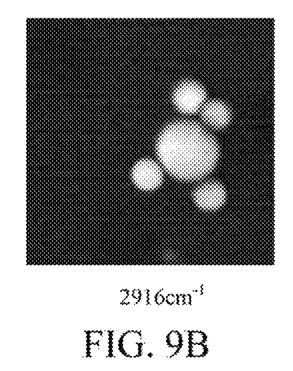
Figure 9C:
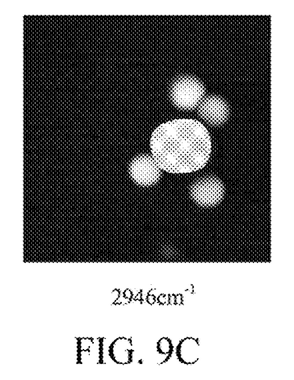
Figure 9D:
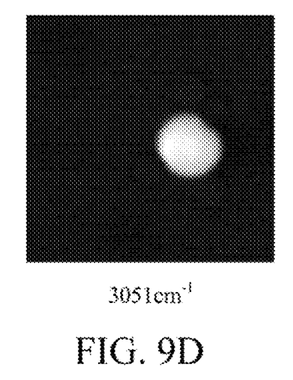

FIG. 8 shows a Raman spectrum of polystyrene (beads each having a diameter of 10 μm) and a Raman spectrum of PMMA (beads each having a diameter of 4 μm), which were detected in experiments using a fast wavelength tunable band-pass filter (TBPF). Moreover, FIGS. 9A to 9D show resulting images of these polystyrene and PMMA. As particularly understood from FIG. 8, detected values (light intensities) of the polystyrene and the PMMA at a light wavenumber of around 2920 $cm^{-1}$ have almost no difference. However, scanning for a vibration frequency corresponding to $W_R$ (corresponding to a light wavenumber of 2800 to 3100 $cm^{-1}$) provided a clear difference between the Raman spectra of the polystyrene and the PMMA, which enabled accurate discrimination and detection of the polystyrene and the PMMA. This experiment used a titanium sapphire laser having a repetition frequency of 76 MHz as the light source for the pump light and used a mode-locked Yb fiber laser having a repetition frequency of 38 MHz as the light source for the Stokes light.

Embodiment 2

Figure 2:
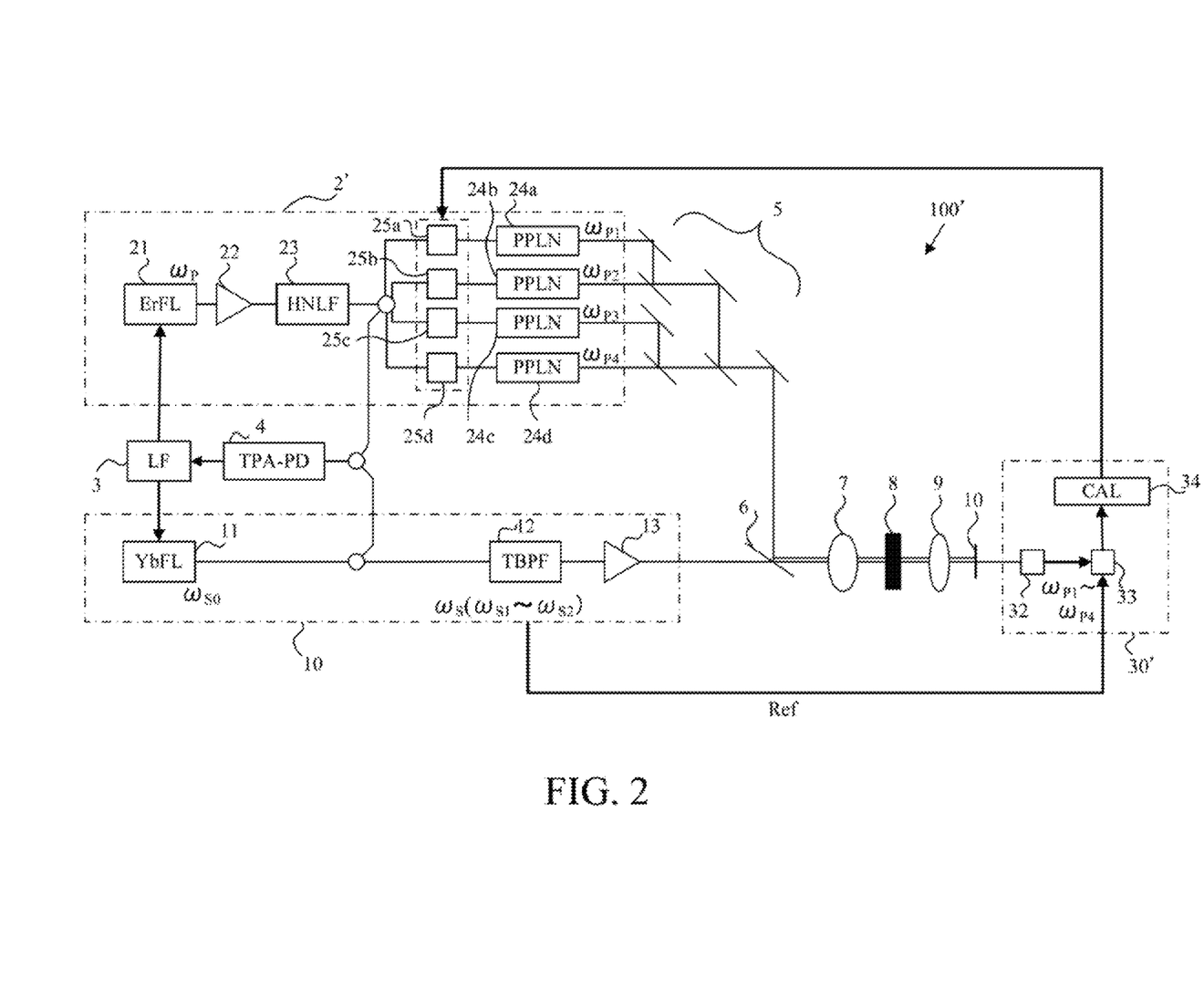
FIG. 2 is a block diagram showing a configuration of a stimulated Raman scattering measurement apparatus that is Embodiment 2 of the present invention.

FIG. 2 shows a configuration of an SRS measurement apparatus 100' that is a second embodiment (Embodiment 2) of the present invention. Components in this embodiment identical to those in Embodiment 1 are denoted by the same reference numerals as those in Embodiment 1, and description thereof is omitted.

Embodiment 1 described the case where the second pulse light generator 2 is configured to cause the plural second pulse lights having the mutually different light frequencies to simultaneously exit therefrom. On the other hand, this embodiment includes a second pulse light generator 2' configured to cause the plural (four as well as in Embodiment 1) second pulse lights having the mutually different light frequencies $\omega_{p1}$, $\omega_{p2}$, $\omega_{p3}$ and $\omega_{p4}$ to sequentially exit therefrom. Specifically, this embodiment provides, between the highly nonlinear fiber 23 and the four PPLNs 24a to 24d, four optical switches 25a to 25d to sequentially select, of the PPLNs 24a to 24d, one PPLN to which the pulse light from the highly nonlinear fiber 23 is introduced.

Moreover, this embodiment provides a light detector 30' including one photodiode 32 and one lock-in amplifier 33 which are used to sequentially detect intensity modulation components of the four second pulse lights (light frequencies of $\omega_{p1}$, $\omega_{p2}$, $\omega_{p3}$ and $\omega_{p4}$) generated by the stimulated Raman scattering. The calculating unit 34 controls ON and OFF of the four optical switches 25a to 25d such that the light frequency $\omega_S$ (from $\omega_{S1}$ to $\omega_{S2}$) of the first pulse light is sequentially scanned with respect to the frequencies of the four second pulse lights. Thus, the calculating unit 34 acquires a molecular vibration image and a Raman spectrum in a continuous and wide light frequency range $W_R$ from output of the one lock-in amplifier 33.

This embodiment requires a longer time to scan the target Raman spectrum range as compared with Embodiment 1 that simultaneously performs the scanning of the light frequency of the first pulse light for the four second pulse lights. However, in this embodiment, intensity of the light focusing to the sample 8 at one scanning is a sum of intensity of the first pulse light and intensity of one of the four second pulse lights, which is lower than a sum of the intensity of the first pulse light and intensities of the four second pulse lights in Embodiment 1. Therefore, this embodiment can acquire the molecular vibration image and the Raman spectrum with a lower intensity light as the light being focused to the sample 8, as compared with Embodiment 1.

Embodiment 3

Figure 3:
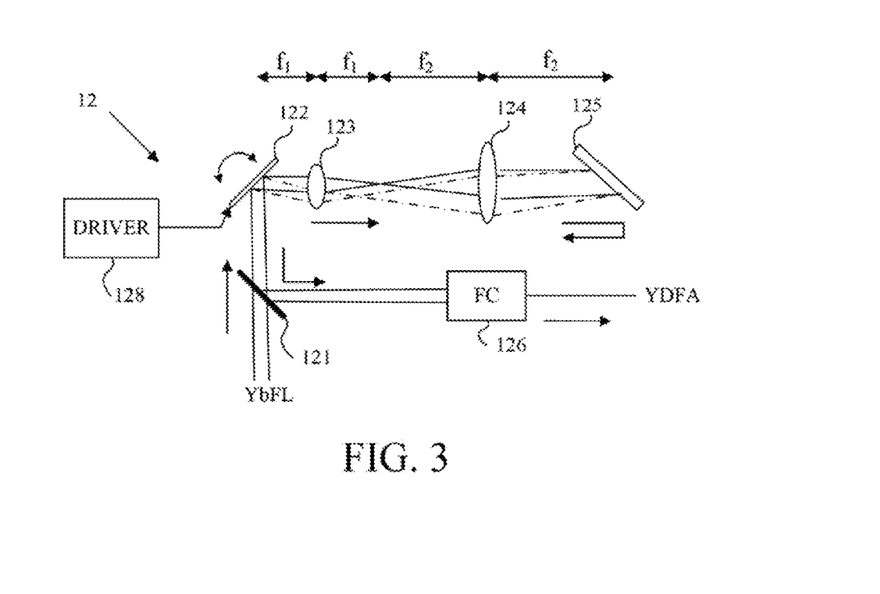
FIG. 3 is a block diagram showing a configuration of a first pulse light generator used in the stimulated Raman scattering measurement apparatus of Embodiment 1.

Next, description will be made of a case of using, as the wavelength tunable band-pass filter 12 in the first pulse light generator 1 described in Embodiments 1 and 2, a wavelength tunable band-pass filter different from that described in Embodiment 1 (FIG. 3).

Figure 4:
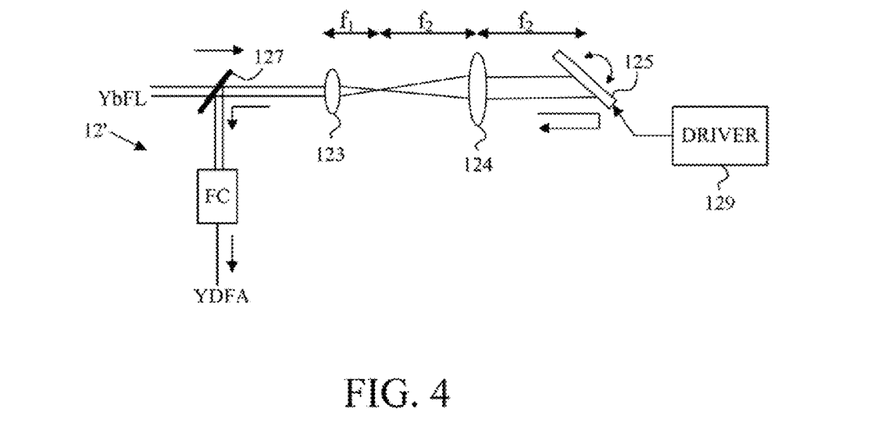
FIG. 4 is a block diagram showing a configuration of a modified example of the first pulse light generator used in the stimulated Raman scattering measurement apparatuses of Embodiments 1 and 2.

For example, a wavelength tunable band-pass filter 12' shown in FIG. 4 uses a half mirror 127 whose angle is fixed, in place of the light deflecting element 122 shown in FIG. 3. The pulse light emitted from the first light source (YbFL) 11 and transmitted through the half mirror 127 enters the light dispersion element 125 through the first and second lenses 123 and 124 as collimated light.

This wavelength tunable band-pass filter 12' rotates (swings) the light dispersion element 125 by the driver 129 to scan the light frequency $\omega_S$ of the first pulse light in the light frequency range from $\omega_{S1}$ to $\omega_{S2}$. The pulse light reflected in the Littrow reflection at the light dispersion element 125 is again transmitted through the second and first lenses 124 and 123, reflected by the half mirror 127 and then collimated by the fiber collimator 126 to exit toward the Yb doped fiber amplifier 13.

In this wavelength tunable band-pass filter 12', in principle, the first and second lenses 123 and 124 may be removed. However, a small diameter of a light beam (pulse light) entering the light dispersion element 125 makes a spectral width of the light progressing to the fiber collimator 126 wide, which may lower the resolution of the Raman spectrum. Therefore, it is desirable to provide the lenses 123 and 124.

Figure 5:
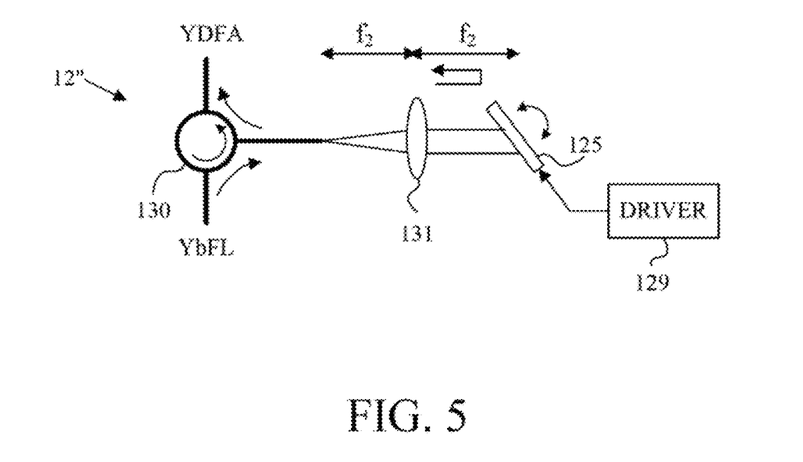
FIG. 5 is a block diagram showing a configuration of another modified example of the first pulse light generator used in the stimulated Raman scattering measurement apparatuses of Embodiments 1 and 2.

Moreover, another wavelength tunable band-pass filter 12" shown in FIG. 5 may be used. The pulse light emitted from the first light source (YbFL) 11 enters a light circulator 130 from its entrance port, exits from an entrance/exit port thereof, is transmitted through a lens 131 whose focal length is f2 and then enters the light dispersion element 125 as collimated light. This wavelength tunable band-pass filter 12" also rotates (swings) the light dispersion element 125 by the driver 129 to scan the light frequency $\omega_S$ of the first pulse light in the light frequency range from $\omega_{S1}$ to $\omega_{S2}$. The pulse light reflected in the Littrow reflection at the light dispersion element 125 enters the light circulator 130 from the entrance/exit port and then exits from an exit port thereof toward the Yb doped fiber amplifier 13.

As described above, it is only necessary that the wavelength tunable band-pass filter be configured to change, by changing an angle of at least one of the light dispersion element that changes the light frequency of the exiting light according to the incident angle of the entering light and the introducing optical system that introduces the light to the light dispersion element, the incident angle to the light dispersion element. The change of the angle of at least one of the light dispersion element and the introducing optical system includes change of the angles of both the light dispersion element and the introducing optical system.

The parameters of the pulse light such as the light frequency, wavelength and repetition frequency described in the above embodiments are merely examples, and other parameters may be used.

Moreover, although the above embodiments described the case of using the diffractive optical element (diffraction grating) as the light dispersion element, other elements may be used as long as they can change the light frequency of the exiting light according to the incident angle of the entering light.

In addition, Embodiments 1 and 2 described the case of producing the plural second pulse lights whose light frequencies are mutually different by using the light emitted from the one second light source provided in the second pulse light generator. However, the second pulse light generator is provided with plural second light sources emitting lights whose light frequencies are mutually different. That is, as the second light source, at least one light source may be provided.

Furthermore, although Embodiments 1 and 2 described the case where the second pulse light generator uses harmonic locking technique, the second pulse light generator is not limited thereto, and an intensity modulator may be used for the second pulse light generator.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-257894, filed on Nov. 25, 2011, which is hereby incorporated by reference herein in its entirety.

What is claimed is:

1. A stimulated Raman scattering measurement apparatus comprising:
    a first light generator configured to produce a first light;
    a second light generator configured to produce a second light having a light frequency different from that of the first light;
    an optical system configured to combine the first light with the second light to focus the combined first and second lights to a sample; and
    a detector configured to detect the first or second light intensity-modulated by stimulated Raman scattering caused by the focusing of the combined first and second lights to the sample,
    wherein the first light generator includes a light introducing optical system and a light dispersion element, the light introducing optical system introducing light to the light dispersion element, and the light dispersion element being operable to separate the light introduced thereto in different directions according to each light frequency,
    wherein the first light generator is configured to drive at least one of the light dispersion element and an optical element included in the light introducing optical system so as to change an incident angle of the light to the light dispersion element to extract part of the separated light by the light dispersion element, thereby being configured to make a light frequency of the first light variable,
    wherein the second light generator is configured to produce a plurality of the second lights having mutually different light frequencies, and
    wherein the apparatus is configured to measure a Raman spectrum by causing stimulated Raman scattering for each of the plurality of second lights by changing the light frequency of the first light.

2. The stimulated Raman scattering measurement apparatus according to claim 1,
    wherein the light dispersion element is an optical element having a diffraction grating.

3. The stimulated Raman scattering measurement apparatus according to claim 1,
    wherein the second light generator includes a highly nonlinear fiber operable to expand a light frequency band of the light and a plurality of harmonic generation elements operable to respectively generate a plurality of harmonics of light components, which have mutually different frequencies, of the light from the highly nonlinear fiber, and
    wherein the second light generator is configured to produce the plurality of second lights by using the plurality of harmonics.

4. The stimulated Raman scattering measurement apparatus according to claim 1,
wherein, when a difference among the light frequencies of the second lights is represented by Wp, a variable width of the light frequency of the first light is equal to or more than Wp.

5. The stimulated Raman scattering measurement apparatus according to claim 1, wherein the second light generator is configured to produce a plurality of the second light having mutually different light frequencies by separating light used for producing the second light into a plurality of light components having mutually different light frequencies.

6. The stimulated Raman scattering measurement apparatus according to claim 1,
wherein the light introducing optical system includes a light deflecting element configured to deflect light toward the light dispersion element and an imaging optical system configured to image the light deflected by the light deflecting element on the light dispersion element.

7. The stimulated Raman scattering measurement apparatus according to claim 1,
wherein the first light is a first pulse light with a first pulse period and each of the plurality of second lights is a second pulse light with a second pulse period which is different from the first pulse period.

8. The stimulated Raman scattering measurement apparatus according to claim 1,
wherein the second pulse period is shorter than the first pulse period and the detector performs synchronous detection with the first pulse period.

9. The stimulated Raman scattering measurement apparatus according to claim 1,
wherein the second light generator is configured to cause the plurality of second lights to simultaneously exit therefrom.

10. The stimulated Raman scattering measurement apparatus according to claim 9,
wherein the detector includes a plurality of detection elements configured to detect light intensity-modulated by stimulated Raman scattering caused for each of the plurality of second lights.

11. The stimulated Raman scattering measurement apparatus according to claim 10,
wherein the detector includes a plurality of amplifiers configured to perform a synchronous detection based on each signal from the plurality of the detection elements.

12. The stimulated Raman scattering measurement apparatus according to claim 11,
wherein the first light is a first pulse light with a first pulse period, each of the plurality of second lights is a second pulse light with a second pulse period which is shorter than the first pulse period, and each of the plurality of amplifiers performs the synchronous detection with the first pulse period.

13. The stimulated Raman scattering measurement apparatus according to claim 1,
wherein the light introducing optical system is configured to introduce collimated light to the light dispersion element.

14. A stimulated Raman scattering measurement apparatus comprising:
a first light generator configured to produce a first light;
a second light generator configured to produce a second light having a light frequency different from that of the first light; and
a detector configured to detect the first or second light intensity-modulated by stimulated Raman scattering caused by focusing the first and second lights to a sample,
wherein the first light generator is configured to make a light frequency of the first light variable,
wherein the second light generator is configured to produce a plurality of the second lights having mutually different light frequencies, and
wherein the apparatus is configured to measure a Raman spectrum by causing stimulated Raman scattering for each of the plurality of second lights by changing the light frequency of the first light.

15. The stimulated Raman scattering measurement apparatus according to claim 14,
wherein the second light generator includes a plurality of harmonic generation elements operable to respectively generate a plurality of harmonics of light components, which have mutually different frequencies, and
wherein the second light generator is configured to produce the plurality of second lights by using the plurality of harmonics.

16. The stimulated Raman scattering measurement apparatus according to claim 15,
wherein the second light generator includes a highly non-linear fiber operable to expand a light frequency band of the light, and
wherein the plurality of harmonic generation elements is configured to respectively generate a plurality of harmonics of light components, which have mutually different frequencies, of the light from the highly nonlinear fiber.

* * * * *